United States Patent [19]

Goodwill

[11] Patent Number: 4,740,077
[45] Date of Patent: Apr. 26, 1988

[54] CENTRIFUGAL MEASUREMENT OF CORE SAMPLES

[75] Inventor: William P. Goodwill, Plano, Tex.

[73] Assignee: Atlantic Richfield Company, Los Angeles, Calif.

[21] Appl. No.: 747,544

[22] Filed: Jun. 21, 1985

[51] Int. Cl.$^4$ .............................................. G01H 15/06
[52] U.S. Cl. ..................................... 356/23; 73/61.4; 356/427
[58] Field of Search ................. 356/23, 427; 250/565; 73/61.4, 38; 382/61

[56] References Cited

U.S. PATENT DOCUMENTS

| | | | |
|---|---|---|---|
| 3,852,573 | 12/1974 | Dolch | 382/61 |
| 4,373,806 | 2/1983 | Tipper | 356/23 |
| 4,567,373 | 1/1986 | O'Meara et al. | 356/427 |

OTHER PUBLICATIONS

Society of Petroleum Engineers SPE 12128 (1983), "Multiphase Relative Permeability Measurements Using an Automated Centrifuge" by D. J. O'Meara Jr. & W. O. Lease.

Primary Examiner—R. A. Rosenberger
Attorney, Agent, or Firm—M. David Folzenlogen; Michael E. Martin

[57] ABSTRACT

An adaptable, accurate, high resolution centrifuge core measuring method using a single strobe flash per measurement uses a microprocessor controller to control the measuring method, not a computer. The controller, not the camera clock, decides when the camera data should be read. The camera data is read into and stored in the controller, not a computer. The controller reads the camera array, controls centrifuge speed, determines alignment of the proper catch tube, flashes the strobe, determines lapse time, rereads the pixels, stores and analyzes the pixel information and the other steps of the method. The controller is capable of operating in many modes. But at any point, for operator intervention the controller is adapted to let the computer intervene.

4 Claims, 2 Drawing Sheets

CENTRIFUGAL MEASUREMENT OF CORE SAMPLES

BACKGROUND OF THE INVENTION

This invention pertains to the measurement of relative permeabilities and capillary pressures by centrifuging natural or synthetic mineral core samples. More particularly, this invention relates to an improved control and data collection system for centrifugal measurement of core samples.

The relative permeabillity and capillary pressure of mineral core samples are measured by centrifuging liquids into or out of the cores. Usually, the core is prepared in a way that it is filled with water or oil; but measurements may be made on cores containing both water and oil and sometimes measurements are made by centrifuging oil or water into a clean core. Normally, the centrifugal measurement of the core sample entails placing the liquid-bearing core sample in a core holder which communicates with a transparent catch tube. The catch tube is also called a collection tube or cup. The tube may or may not be graticulated. The catch tube may or may not be encased in an opaque outer holder which is narrowly slotted for light transmission through the catch tube. Usually, four or six coreholders are used per centrifuge. The core holders are placed in a centrifuge and spun at a fairly precise speed or at different speeds. Speeds up to 20,000 rpm are used. Most of the time the core is spun in a way that the catch tube extends outward, but there are times when an inside spin is desirable.

The major drawbacks to widespread use of the centrifuge is the difficulty of obtaining good data, especially the start of a relative permeability measurement which liquid production is rapid, and also the tedium associated with obtaining good data. It has been proposed, for example, in an article entitled "Multiphase Relative Permeability Measurements Using An Automated Centrifuge" by D. J. O'Meara, Jr. and W. 0. Lease, Society of Petroleum Engineers of AIME, SPE 12128 (19083), to use an automated centrifuge to make relative permeability and capillary pressure core measurements. This centrifugal measuring system uses a special type camera with a specially arranged photodiode array to take pictures, at pre-set times, of the catch tube whose motion is frozen by a strobe light system. A linear array camera is also called a line scan camera. A linear array is a very narrow line of very small photodiodes about an inch long. The photodiodes act as small capicitors, each storing a charge which is proportional to the amount of light impinging on its surface. Each photodiode yields one "picture element" (pixel). The diodes are on a spacing as as small 1728 photodiodes in a linear inch, that is, less than one mil in spacing. This enables measurement of a phase boundary or liquid interface to a few thousandths of the volume of the catch tube. For centrifuge measurements, a camera lens system allows this small length array to see up to about three inches. The pixel information of the camera is a series of light dependent voltages which depend on the amount of light seen by each diode. A significant difference between this earlier automated system and this invention concerns the camera operation. The camera has a clock which reads the photodiode data very rapidly in sequence. Reading of the camera pixels is accomplished with a solid state switch. The earlier automated system was synchronized on the camera clock. In a sense, the camera clock says that its is ready to send data and then it reads out the data by way of solid state switch. Thus, in one way, the earlier automated system timing was controlled by the camera. This is undesirable.

The strobe lamp is placed in line with the catch tube path and at one side of the centrifuge. Usually, the strobe lamp is laid on the bottom side of the centrifuge. The linear photodiode array of the camera is also placed in line with the catch tube path and on the opposite side of the centrifuge. Usually there is an aperature in the top of the centrifuge for the camera lens. The camera sees some background light until the strobe lamp is flashed. Even in a dark centrifuge, there is background light and dark current noise which the camera detects and accumulatively collects until the next flash. Some centrifuges have transparent plastic tops so that the background light may be appreciable. This is significant because the earlier automated system requires more than one light flash per measurement. Compounding the background light by multiple flashes per measurement creates noise that obscures measurement of a liquid interface inside the catch tube.

The strobe lamp is flashed on command when the position of the catch tube is in line with the camera and strobe lamp. The strobe flash transmits light through the catch tube to the camera. The amount of light transmitted through the tube is detected by the thousand or more individual pixels in the linear array. One key factor in accurately and rapidly measuring the position of the liquid interface in the catch tube is the uniformity and intensity of the light and the number of flashes it takes to make a measurement. A typical strobe lamp uses a circular reflector with discrete flat reflector surfaces designed to cause the light to be concentrated into a circular pattern. A standard lamp causes noise and hot spots. The camera internal electronics tend to saturate during hot spots. This reduces contrast. In the previously suggested automated centrifuge system, the standard strobe lamp caused the camera to detect not only the tube image, but also a hot spot of light emanating from the strobe bulb. The earlier automated system attempted to resolve this problem by imbedding two strobe bulbs in a piece of plexiglass which placed the strobe bulbs off a direct line of sight from the camera. The plexiglass was heavily sandblasted to give a pebbly surface which was then painted reflective white. Even with this two bulb strobe lighting system, it was necessary to enhance the liquid interface by floating light-diffracting materials on the interface. For this two bulb strobe system, it also was necessary to use presicion bore glass collection tubes of square cross section. The square cross section was designed to provide surfaces of fairly uniform illumination over the tube width and to reduce the effects of variation in strobe timing that inherently occur. In the earlier automated system, standard round catch tubes acted as a lens concentrating all of the strobe light in a very narrow band along the major axis. This decreased the area over which the photodiode array of the camera was effective. If the camera was initially focused on the bright line down the middle of the tube caused by the lens effect, then any offset in the strobe light caused under-exposure of the photodiodes and hence, a complete loss of image. Moreover, it was necessary to strobe the catch tube at least three times or more to produce a good image. The number of multiple strobe flashes was set at the beginning of the run and was not changed during the run. This compounds noise problems and variations in centrifuge speed.

It would be highly desirable to have an improved computerized centrifuge measuring system that does not require multiple strobe flashes, light-deffracting materials, two strobe lights or catch tubes of square cross section.

In the earlier automated system, a computer controls the measurement and a controller only carries out the computer command as to speed and taking the image. This is undesirable. The speed control task is set on twelve bits of two parallel input-output ports which are monitored by the controller. The twelve bit speed demand of the computer is translated by a digital-to-analog converter in the controller into a fixed DC voltage. This voltage is a set point against which the controller continually compares the centrifuge speed. The speed is obtained from a pulse type signal derived from measuring the light passing through twenty holes on the circumference of a speed disk which is attached to the centrifuge motor shaft. The resulting error is translated into a voltage correction which is sent to the motor via the speed set point line. It is desirable to provide an improved and different way of controling, varying and changing the speed of the centrifuge. For example, it is desired to more accurately and frequently determine the speed and orientation of the centrifuge arms without the requirement of a computer separate from the controller.

As previously mentioned, in the previously suggested automated measuring system, the task of obtaining an image results only from strobing the collection tube of interest for a specified multiple number of three or more times. The request for an image is controlled by a computer which sends a command to the controller to take an image and have it delivered to the computer. Also as previously stated, the controller is synchronized to the camera clock and solid state switch which reads out the camera data when the camera is ready. In other words, the camera is not controlled by the controller. The controller knows when the collection tube of interest is in line with the camera by monitoring an index mark on a speed disk with twenty tube orienting holes in it. The mark shows up once per revolution of the disk and the holes are counted. When the proper hole is in line, the controller strobes this tube the required multiple number of times. Regardless of speed controls, the speed of the centrifuge varies. Even if the variation is slight, slight changes affect alignment of the strobe, catch tube and camera with each flash. Multiple flashes and slight speed changes affect image clarity and accuracy. This is compounded by use of holes to detect alignment.

In the earlier automated system, as soon as the first camera pixel starts to send its voltage to the computer the controller sends a valid data line high. This initiates an assembly language program to read pixel voltages into the computer on an analog-to-digital converter. The program reads data at exactly the camera clock frequency. It is noted that in the earlier system, the camera data is read into the computer not the controller. This ties up the computer and is undersirable.

Of the two core measurements usually conducted on cores, relative permeabiity is the more exacting. Relative permeability is measured by spinning the core holder at a high enough speed to overcome capillary effects in the core. Liquid is produced from the core into the catch tube and the amount of production is measured as a function of time. Relative permeability measurements, therefore, are concerned with the shape of a relative volume/time dependent graphical or mathematical curve. This requires rapid data taking, especially at the start of the relative permeability measurement. For increased accuracy and other reasons, it is desirable that the centrifuge system enable rapid taking of data. Rapid accurate data taking is available only if the time to take a measurement is relatively short. It is a purpose of this invention to provide such a system.

Capillary pressure experiments involve increasing the centrifuge speed at which the core is rotated in steps and measuring the steady-state liquid production at each step. Steady-state data taking can take relatively long periods of time. It is tedious and it generates a lot of unnecessary data which in the earlier automated system filled the storage capacity of the computer since the data was delivered directly to the computer.

SUMMARY OF THE INVENTION

This invention provides a very adaptable, accurate, high resolution centrifuge core measuring method using a single strobe flash per measurement.

This method uses a microprocessor controller to control the measuring system, not a computer. In this method, the controller, not the camera clock, decides when the camera data should be read. The camera data is read into and stored in the controller, not a computer. The controller reads the camera array, controls centrifuge speed, determines alignment of the proper catch tube, flashes the strobe, determines lapse time, rereads the pixels, stores and analyzes the pixel information and the other steps of the method. The controller is capable of operating in many modes. But at any point, for operator intervention the controller is adapted to let the computer intervene.

Briefly, the method of this invention involves accurately determining centrifuge speed before each liquid interface measurement and also erasing the camera before each measurement, thereby assuring more accurate alignment of the catch tube with the strobe and camera and reducing background light accumulation in the camera. Thereafter, there is calculated when the desired catch tube, strobe and camera will be aligned. After the proper time has elapsed, the strobe is flashed only once for each measurement. The camera is triggered to read the pixel information which is stored directly in the controller. There is detected reference and interface position and the number of pixels therebetween. Stored in the controller is catch tube identification, the number of pixels between the reference and interface, centrifuge speed in rpm, and the elapsed time of day at that moment.

This improved automated system is very accurate. It has high resolution. The elapsed time of day resolution for each mearsurement taken is ten milliseconds over a period of one month. It primarily relies on and is controlled by a controller, thereby freeing a computer to perform other functions. Many controllers may attached to one computer.

The improved centrifuge core measuring system is very adaptable to many variations. It can adjust the firing trigger for the single strobe flash for instantaneous centrifuge rpm. It can determine if the reference mark, interface and number of pixels conforms to recognized patterns. If either is not recognized, it can delete the information and quickly retake the measurement until the information is recognized or until a preset number of attempts has been made. It can compare data with previous reading and eliminate unnecessary data. This condenses the data to be stored. It can call the computer when its storage reaches a predetermined level. It can surrender itself to a computer to permit operator intervention or periodic checks, thereby avoiding loss of time due to malfunctions.

DETAILED DESCRIPTION OF PREFERRED EMBODIMENTS

Figure 1:
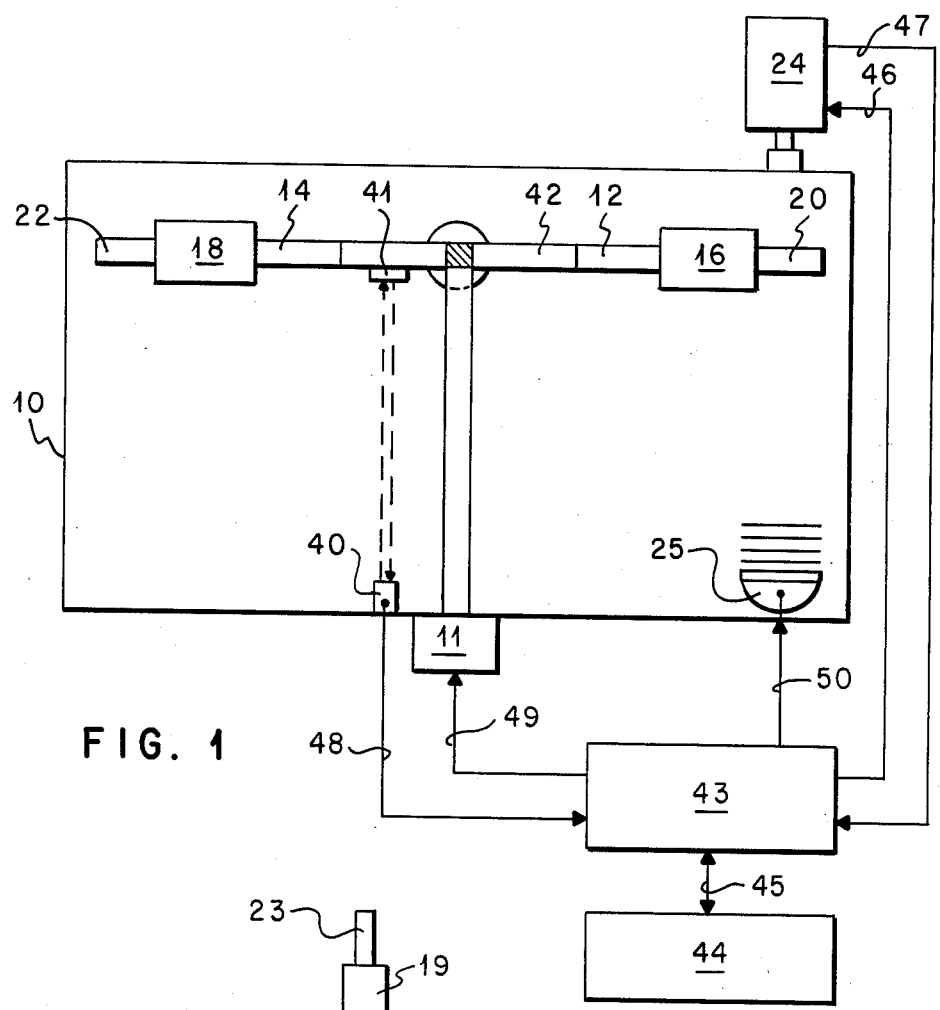
FIG. 1 is schematical view of the centrifuge core measuring system of this invention.

This invention provides an improved controlled core measuring system. The core measuring system may be better understood by having reference to the drawings wherein in FIG. 1 there is illustrated centrifuge 10. The type of centrifuge is not a part of this invention. It is an off-the-shelf centrifuge suitable for this invention. The centrifuge is capable of operating at the desired speeds and having its speed adjusted by the voltage applied to the motor of the centrifuge. For development of this invention, a Beckman L5-50P which operates at speeds up to 20,000 rpm and a Beckman J-6B which operates over a speed range of 100 to 5,000 rpm were used. If different centrifuges are used, they will generally be similarly retrofitted with additional hardware and used in conjunction with similar software. The software used in this invention is coventional, time critical and uses pattern recognition algorithms. The software, therefore, will not be described in detail. Centrifuge 10 has motor 11 which is adapted to rotate at a speed dependent on the voltage applied to the motor. The centrifuge has an even number of arms 12, 13, 14 and 15 and core holders 16, 17, 18 and 19 and catch tubes 20, 21, 22 and 23, respectively. For illustrative purposes, only four arms are shown, but there may be six or more even number of arms. These features of the centrifuge are standard.

Centrifuge 10 is reftrofitted with conventional linear array camera 24 and special strobe lamp 25. A linear array camera has been previously described. The special strobe lamp is formed in the manner set forth in copending application Ser. No. 747,545, filed on even date herewith and entitled "Centrifuge Strobe Lamp Holder", now U.S. Pat. No. 4,675,791, and owned by a common assignee. The special strobe lamp permits the catch tube to be flashed only once per measurement without the use of floating light-diffracting materials and special square crosssection catch tubes. The strobe lamp holder has a member with length and width. The strobe lamp holder has light confining reflective sections and a curved inner reflective surface. The light confining reflective end sections and reflective curved inner surface confine and concentrate the light from a strobe bulb and are adapted to cause the holder to emit light in a substantially rectangular pattern. The length of the rectanglar pattern is designed to be parallel to the major axis of a catch tube when the strobe lamp is used in a centrifuge core measuring system. The strobe lamp has a diffusive layer through which the light is transmitted. The diffusive layer coacts with the rectangular light pattern and spreads the captured and reflected light rays uniformly across the rectangular light pattern thereby virtually eliminating interfering bright spots. These features of the improved strobe lamp holder cause the light diverging from a strobe bulb to impinge on the reflective surfaces which reflects the light from the strobe bulb in a uniform manner from one side of the curved inner surface of the segment to the other side of the segment. The light rays are transmitted from the lamp in a side to side line in a narrow rectanglar pattern with the light rays acting as though they were oriented to be parallel to the major axis of a centrifuge transparent catch tube. The improved light intensity, uniformity, orientation and configuration enhances detection and measurement of a liquid interface inside the catch tube and of graticulate reference marks on the catch tube with a single strobe flash and with improved accuracy and resolution.

Figure 3:
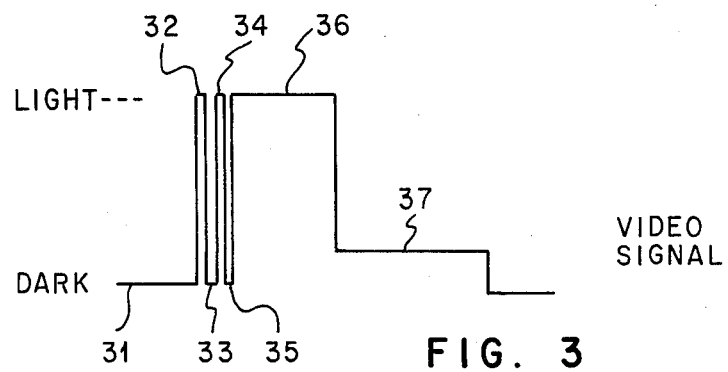
FIG. 3 is schematical view illustrating the video information generated by a single strobe flash and illustrating how catch tube reference marks and liquid interface are used to determine liquid volume in the catch tube.
Figure 4:
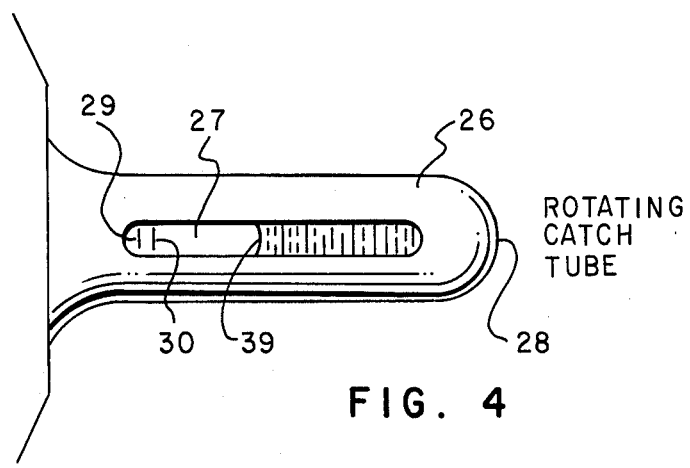
FIG. 4 is a schematical view of a catch tube inside a slotted opaque catch tube holder.

As shown, strobe lamp 25 is laid on the bottom of the centrifuge. The strobe lamp is positioned to be in line with the linear array of camera 24 with the length of the rectanglar light pattern of the strobe lamp parallel to the camera line scan array. The camera array and the length of the rectangle of the strobe lamp are also positioned and aligned to be in line with and parallel to the major axis of each catch tube as they rotate between the camera and strobe lamp. The method of this invention is suitable for use with any type of catch tube; but at high speeds, the catch tube is usually inside opaque cup holder 26 of FIG. 4. The cup holder is slotted on both sides with slot-like elongated window 27 through which light is transmitted from strobe lamp 25 to the linear array of camera 24. As specially noted, the catch tube and cup holder 26 may be made round. There is no need for square cross section catch tubes. This invention uses a reference mark when taking a measurement. The end of catch tube (not shown) may be used as a reference mark, but the end is not a clean cut reference mark. In addition, an opaque cup holder hides the end of the catch tube. One of the end edges of window 27 may be used as the reference mark when cup holder 28 is not used, but for improved operation it is preferred to use a cleaner more recognizable reference marking. Accordingly, in FIG. 4, the catch tube has reference marks 29 and 30. This provides clearer and better pattern recognition since as shown in FIG. 3 the photodiodes of camera 24 see dark segment 31, light segment 32, dark segment 33, light segment 34 and dark segment 35. This identifies the reference mark. As shown, this is followed by light segment 36 and reduced and different light segment 37. As hereinafter mentioned, the number of photodiodes represented by light segment 36 determines the location of liquid interface 39.

Figure 2:
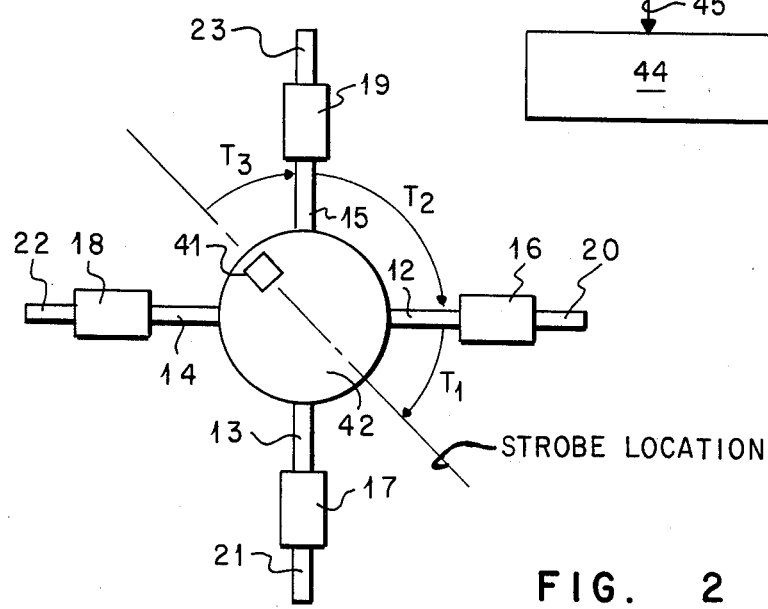
FIG. 2 is a schematical view of four centrifuge arms and a pickoff to illustrate how catch tube position is calculated.

Centrifuge 10 is also retrofitted with means adapted to detect the beginning and end of a revolution of the catch tube assembly. As shown in FIG. 1, this is accomplished with photoelectric transmitter/receiver 40. Transmitter/ receiver 40 acts in conjunction with reflector 41. The reflector may be located anywhere on the rotating part of the centrifuge. In FIG. 2, it is shown mounted on central disk 42 from which the arms of the core holders extend.

Centrifuge 10 also works in conjunction with and is controlled by controller 43 which is a versatile, high storage microprocessor controller. Controller is designed in the usual fashion to be controlled by optional computer 44 via hookup 45. Normally computer 44 will not be involved in the taking of measurements. It is placed in use only when controller 43 calls it in order to read out its data storage into the computer. The computer may also be used when it is desirable to override the controller or to check how things are going. The software enables the computer to in effect ask the controller if everything is going alright. Accordingly, in this method, the controller controls the measuring system, not a computer. In this method, the controller, not the camera clock, decides when the camera data should be read. The controller is adapted to send a signal via line 46 to the solid state switching network of camera 24 to cause the switching network to read out the pixel voltages into line 47 which delivers the thousand or so readings to the controller. The camera data, therefore, is read into and stored in the controller, not a computer. Controller 43 is also adapted to receive via line 48 each pulse created by receiver/transmitter 40. The controller has various clocks. One acts in conjuction with the receiver/transmitter and reads the time between two pulses from the receiver/transmitter, thereby determining the speed of the centrifuge. The controller also determines the speed of the centrifuge by sending the proper voltage to motor 11 via line 49. The controller is also adapted to determine alignment of the proper catch tube. This is accomplished without the use of holes or other indexing marks on the centrifuge other than reflector 41. The controller simply detects when reflector 41 is in line with transmitter/receiver 40 and then in conjunction with the speed of the centrifuge adds the time it takes for the centrifuge to rotate the desired distance or angle for the desired catch tube to be in line with the camera and strobe lamp. The angle or degrees stays constant. Only the centrifuge speed changes. For example, if catch tube 23 is to be measured, then as depicted in FIG. 2, the controller adds the time needed for catch tube to travel distances $T_1$ and $T_2$. The total time is made of time $T_1$ during which catch tube 20 lines up with the strobe and camera and time $T_2$ which is a quarter of a revolution during which catch tube 23 lines up with the strobe and camera. In the foregoing example, in the direction of rotation, the travel time $T_3$ from reflector 41 to catch tube 23 is the same as the travel time $T_1$ for catch tube 20 to reach the point where the strobe lamp and camera line up, but it is not necessary for reflector 41 to be so located.

When the desired catch tube is lined up with the strobe lamp and camera, the controller by way of line 50 flashes strobe lamp a single time to take a measurement. It is important to note that only one flash per measurement is used.

As previously stated the controller is then adapted to read the camera pixel information via lines 46 and 47 directly into the controller. The controller searches for reference points 32, 33, 34 and 35 the beginning of segment 37 in FIG. 3 which designates the interface position 39 and calculate the number of pixels represented by the length of segment 36. The volume in the catch tube between reference mark 35 and the end of the catch tube is constant and proportional to the length of the catch tube between the reference mark and the end of the catch tube. Similarly, the volume in the catch tube between the interface location and the end of the end of the catch tube is proportional to the length of the distance between the interface and the end of the catch tube. Thus, the controller can readily calculate the volume of the liquid in the catch tube by substracting the length of the pixels represented by segment 36 from the constant length of the catch tube beyond reference mark 30. The controller is also adapted to make and store a time dependent list of the catch tube identification (e.g. 20, 21, 22, or 23), the number of pixels between reference mark 30 and interface 39, the centrifuge speed in rpm, and elapsed time of day at that moment. If the reference mark, interface and number of camera pixels are not recognized, the controller may be adapted to repeat the measurement until a valid set of data is recognized or until a preset number of attempts have been made, whichever comes first.

Figure 5:
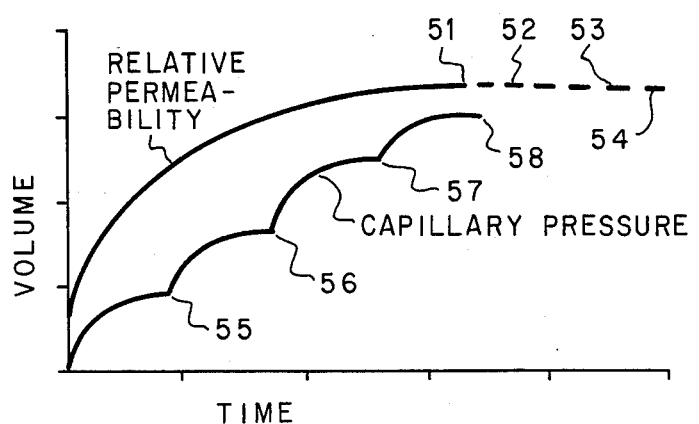
FIG. 5 is a graphical illustration of the relative permeabilty and capillary pressure data and illustrates how the data may be condensed.

In FIG. 5, the measurements taken when measuring relative permeability and capillary pressure are represented graphically.

Relative permeability is measured by spinning a core holder at a high enough speed to overcome capillary effects in the core. Liquid is produced from the core into the catch tube and the amount of production is measured as a function of time. Relative permeability measurements, therefore, are concerned with the shape of a relative volume/time dependent graphical or mathematical curve. This requires rapid data taking, especially at the start of the relative permeability measurement. Data points where there is little or no change in volume (interface position) are of little value, yet the unit must be run until equilibrium is assured. In the curve shown, there is practically no change after point 51. The controller may be adapted to compare reading 51 with reading 52. If the change is less than a predetermined amount, the controller may discard data point 52 and similarly data points 53 and 54. This illustrates how the controller may be adapted to condense the data. After a predetermined time or number of data points without change have been experienced, the controller may be adapted to inform the operator that the test is complete.

Capillary pressure experiments involve increasing the centrifuge speed at which the core is rotated in steps and measuring the steady-state liquid production at each step. These steps are represented in FIG. 5 by points 55, 56, 57, and 58. The controller may be adapted to determine when the readings cease to vary thereby indication steady state and to increase the centrifuge speed by the desired amount. It may also be adapted to discard data points that were between readings 55, 56, 57 and 58. The controller may also be adapted to call computer 44 when the storage in the controller reaches a predetermined amount.

In operation, after the cores have been prepared and placed in centrifuge 10, the experiment is started with zeroing of the elapsed time clock in the system. As previously mentioned, the clock generates 100 counts per second. The desired centrifuge speed is preset. Controller 44 monitors this speed. It has a digital to analog converter and controls the motor speed by sending voltage over line 49 to motor 11. The speed is read by determining the start of a revolution. This is available from the pulse sent to the controller whenever transmitter/receiver 40 receives a reflection from reflector 41. At the same time the controller starts a timer. Then the controller via the software notes the next pulse from the reflector and stops the same timer. The measured time (to the nearest four microseconds) is the time for one revolution and is inversely proportional to rpm. The centrifuge speed is determined before each strobe flash. This assures better data.

The controller calculates time delay for the desired catch tube to line up with a strobe light source and a line scan camera having a linear array of photodiode pixels in a number at least sufficient to provide readings to the desired degree of accuracy. A photodiode array of 1728 diodes per inch is preferred, but a smaller number may be used. The software waits for a revolution two times for stability. Centrifuge speed does vary even though controlled by digital to analog signals from the controller. But speed is fairly stable for three revolutions unless rapidly accelerating or decelerating. It divides the time for one revolution by the number of core holders, usually 4 or 6. Working in conjunction with reflector 41, the controller uses this time to determine when the catch tube to be measured is in line with the camera and strobe lamp. For example, if catch tube 23 is to be measured, then as depicted in FIG. 2, the controller adds the time needed for catch tube to travel distances $T_1$ and $T_2$. The total time is made of time $T_1$ during which catch tube 20 lines up with the strobe and camera and time $T_2$ which is a quarter of a revolution during which catch tube 23 lines up with the strobe and camera. The time is to the nearest four microseconds which is less than 1° even at the fastest centrifuge speed of 20,000 rpm.

Before flashing the strobe, the controller reads the camera pixels and discards the readings. It takes about 20 milliseconds to read out the camera. This erases the camera pixel voltages reducing the charge of accumulated noise. Thereafter, the controller flashes a single strobe bulb in strobe lamp 25 in synchronization with the catch tube to be measured in a manner and at a time which places the desired catch tube in line with the strobe lamp and linear array of camera 24 at the instant the single strobe bulb is flashed. The strobe bulb is flashed only once for each measurement.

The controller reads camera pixel data from said camera into a data memory of the controller, preferably for reasons hereinafter made more apparent a raw data memory. In this invention, the solid state switch of the camera is clocked by the controller. When the controller wants to read camera pixels, it sends out a clock pulse every 12 microseconds telling the camera to send one picture element. The controller digitizes the analog camera information. Black is zero and white is full on. The values between zero and full on represent shades of grey. Once digitized, the controller searches for the reference points 32, 33, 34 and 35 and for the position interface 39 and calculates the number of pixels between reference point 35 and interface 39. Preferably, the controller uses conventional pattern recognition alogarithms to search for the shaped of the reference marks of the catch tube and the liquid interface. This is enhanced by the types and series of marks used. If the reference mark, the interface and/or the number of camera pixels are not recognized, the controller repeats the measurement until the reference mark, the interface and the number of camera pixels are recognized unless the reference mark, the interface and the number of camera pixels are not recognized within a predetermined number of number of repeats, usually three to seven repeats. If multiple interfaces are present, the controller determines which interfaces are to be searched for and stored. This is a further advantage of the use of pattern recognition. Up to twelve interfaces may be recognized and stored.

The controller stores into a data storage buffer of the controller the identification of the catch tube measured, the number of pixels, the centrifuge speed in rpm, and the elapsed time of day at that moment. Preferably, the total information is stored in a total of nine 8-Bit memory locations in the controller. The above procedure is repeated for each catch tube in the centrifuge which is to be measured. After each catch tube is measured, the controller waits until time to take another set of measurements of each catch tube and therafter the procedure is repeated until completion of the core measurement.

Other modifications and variations obvious to those skilled in this art may be used. For example, a computer may error check the controller at any time or the computer may be take over the operation of the measurement at any time. The controller is a stand alone unit with lots of memory and several controllers may be used in conjunction with one computer and still allow the computer to perform other functions.

What is claimed is:

1. A method for measuring the level of a liquid interface in a centrifuge catch tube while said catch tube is being rotated by a centrifuge comprising:

providing a centrifuge having at least one rotating arm means adapted to support an elongated centrifuge catch tube for rotation about an axis at a relatively constant speed, said centrifuge including a strobe light source, a line scan camera supported spaced from said light source so that said catch tube passes betwen said light source and said camera, said line scan camera having a linear array of photodiode pixels of a number at least sufficient to permit measurement of the location of a liquid interface in said catch tube, said catch tube having at least one reference mark disposed thereon to be sensed by said camera, a microprocessor controller adapted to read said camera pixels, discard said readings and reset said pixels for a further reading, said controller being operable to control centrifuge speed, determine alignment of said catch tube in a predetermined position between said strobe light source and said camera and control said strobe light source, and a computer operably connected to said controller and adapted to receive data from said controller, and with said controller;

before each measurement of said level of said interface, determining the start of a revolution of said catch tube and the end of said revolution and measuring the elapsed time of said revolution to determine rotational speed of said catch tube;

determining the time for said catch tube to align with said strobe light source and said camera while rotating from a reference point with sufficient accuracy to permit measurement of the location of a liquid interface with respect to said reference mark;

flashing said strobe light source in synchronization with said catch tube in a manner which places said catch tube in line with said strobe light source and said camera so that said camera may perceive said interface;

transferring signals from said camera pixels into said controller;

repeating the reading of signals from said camera pixels a predetermined number of times until signals indicating the location of said reference mark and said interface are present to determine the location of said liquid interface relative to said reference mark so that a measurement of volume of liquid accumulated in said catch tube may be determined for measuring the relative permeability of substance and the like; and comparing said measurement of said interface to a previous measurement of said interface for said catch tube to determine the change in location of said interface relative to said reference mark and ignoring a later reading of said location of said interface if the change in said location of said interface is less than a predetermined amount.

2. The method set forth in claim 1, including the steps of:

comparing a measurement of the location of said interface relative to said reference mark of said catch tube to a preious measurement to determine the amount of change in location of said interface; and increasing the speed of said centrifuge a predetermined amount when the change in location of said interface is below a predetermined amount relative to said reference mark for a predetermined number of measurements.

3. A method for measuring the level of a liquid interface in a centrifuge catch tube while said catch tube is being rotated by a centrifuge comprising:

providing a centrifuge having at least one rotating arm means adapted to support an elongated centrifuge catch tube for rotation about an axis at a relatively constant speed, said centrifuge including a strobe light source, a line scan camera supported spaced from said light source so that said catch tube passes between said light source and said camera, said line scan camera having a linear array of photodiode pixels of a number at least sufficient to permit measurement of the location of a liquid interface in said catch tube, said catch tube having at least one reference mark disposed thereon to be sensed by said camera, and a microprocessor controller adapted to read said camera pixels, discard said readings and rest said pixels for a further reading, said controller being operable to control centrifuge speed, determine alignment of said catch tube in a predetermined position between said light source and said camera and control said light source, and with said controller;

before each measurement of said level of said interface, determining the start of a revolution of said catch tube and the end of said revolution and measuring the elapsed time of said revolution to determine rotational speed of said catch tube;

determining the time for said catch tube to align with said light source and said camera while rotating from a reference point with sufficient accuracy to permit measurement of the location of a liquid interface with respect to said reference mark;

flashing said light source in synchronization with said catch tube in a manner which places said catch tube in line with said strobe light source and said camera so that said camera may perceive said interface;

transferring signals from said camera pixels into said controller;

reading signals from said camera pixels to determine the location of said liquid interface relative to said reference mark so that a measurement of volume of liquid accumulated in said catch tube may be determined for measuring the relative permeability of substances and the like;

comparing a measurement of the location of said interface relative to said reference mark of said catch tube to a previous measurement to determine the amount of change in location of said interface; and increasing the speed of said centrifuge a predetermined amount when the change in location of said interface is below a predetermined amount relative to said reference mark for a predetermined number of measurements.

4. A method for measuring the level of a liquid interface in a centrifuge catch tube while said catch tube is being rotated by a centrifuge comprising:

providing a centrifuge having at least one rotating arm adapted to support generally cylindrical elongated centrifuge catch tube for rotation about an axis at a relatively constant speed, said centrifuge including a strobe light source having a single strobe bulb, a line scan camera supported spaced from said light source so that said catch tube passes between said light source and said camera, said line scan camera having a linear array of photodiode pixels of a number at least sufficient to permit measurement of the locations of a liquid interface in said catch tube, said catch tube having at least one reference mark disposed thereon to be sensed by said camera, and a microprocessor controller adapted to read said camera pixels, discard said readings and reset said camera pixels for a further reading, said controller being operable to control centrifuge speed, determine alignment of said catch tube in a predetermined position between said strobe light source and said camera and control said strobe light source, and with said controller;

before each measurement of said level of said interface, determining the start of a revolution of said catch tube and the end of said revolution and measuring the elapsed time of said revolution to determine rotational speed of said catch tube;

determining the time for said catch tube to align with said strobe light source and said camera while rotating from a reference point with sufficient accuracy to permit measurment of the location of a liquid interface with respect to said reference mark;

flashing said strobe light source in synchronization with said catch tube only once per revolution of said catch tube and in a manner which places said catch tube in line with said strobe light source and said camera so that said camera may perceive said interface;

transferring signals from said camera pixels into said controller;

reading signals from said camera pixels to determine the location of said liquid relative to said reference mark so that a measurement of volume of liquid accumulated in said catch tube may be determined;

comparing said measurement of said interface to a previous measurement of said interface for said catch tube to determine the change in location of said interface relative to said reference mark and ignoring a later reading of said location of said interface if the change in said location of said interface is less than a predetermined amount;

comparing a measurement of the location of said interface relative to said reference mark to a previous measurement to determine the amount of change in location of said interface; and increasing the speed of said centrifuge a predetermined amount when the change in location of said interface is below a predetermined amount relative to said reference mark for a predetermined number of measurements.

* * * * *